United States Patent [19]

Arrowsmith et al.

[11] Patent Number: 4,891,372

[45] Date of Patent: Jan. 2, 1990

[54] ANTIARRHYTHMIC AGENTS, COMPOSITIONS AND METHOD OF USE THEREAS

[75] Inventors: John E. Arrowsmith, Deal; Peter E. Cross, Canterbury, both of England

[73] Assignee: Pfizer Inc., New York, N.Y.

[21] Appl. No.: 170,499

[22] Filed: Mar. 21, 1988

[30] Foreign Application Priority Data

Mar. 25, 1987 [GB] United Kingdom ............... 8707120

[51] Int. Cl.$^4$ ............... C07D 223/16; A61K 31/55
[52] U.S. Cl. ............................ 514/213; 540/594
[58] Field of Search ..................... 540/594; 514/213

[56] References Cited

U.S. PATENT DOCUMENTS

| | | | |
|---|---|---|---|
| 3,341,584 | 9/1967 | Larsen et al. | 260/556 |
| 3,478,149 | 11/1969 | Larsen et al. | 424/228 |
| 3,574,741 | 4/1971 | Gould et al. | 260/556 |
| 3,660,487 | 5/1972 | Larsen et al. | 260/556 A |
| 3,758,692 | 9/1973 | Larsen et al. | 424/321 |
| 4,210,749 | 7/1980 | Shetty | 542/469 |
| 4,233,217 | 11/1980 | Shetty | 540/494 |

FOREIGN PATENT DOCUMENTS

| | | |
|---|---|---|
| 0131302 | 1/1985 | European Pat. Off. |
| 0164865 | 12/1985 | European Pat. Off. |
| 0200455 | 4/1986 | European Pat. Off. |
| 0204349 | 5/1986 | European Pat. Off. |
| 1268243 | 3/1972 | United Kingdom |

Primary Examiner—David B. Springer
Attorney, Agent, or Firm—Peter C. Richardson; Paul H. Ginsburg

[57] ABSTRACT

An antiarrhythmic agent of the formula

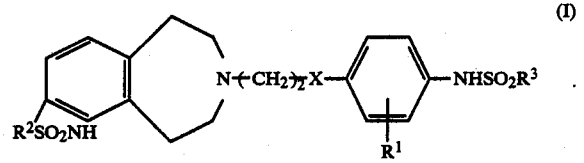

or a pharmaceutically acceptable salt thereof; wherein
$R^1$ is H, $C_1$–$C_4$ alkyl or $C_1$–$C_4$ alkoxy;
X is O,

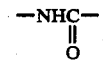

or a direct link; and
$R^2$ and $R^3$, which are the same or different, are each $C_1$–$C_4$ alkyl, with the proviso that when X is

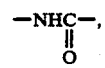

$R^2$ and $R^3$ are the same.

21 Claims, No Drawings

ANTIARRHYTHMIC AGENTS, COMPOSITIONS AND METHOD OF USE THEREAS

This invention relates to certain benzazepine sulfonamides which are antiarrhythmic agents, and to intermediates therefor.

The antiarrhythmic compounds of the invention prolong the duration of the action potential in cardiac muscle and conducting tissue, and thereby increase refractoriness to premature stimuli. Thus, they are Class III antiarrhythmic agents according to the classifications of Vaughan Williams (Anti-Arrhythmic Action, E. M. Vaughan Williams, Academic Press, 1980). They are effective in atria, ventricles and conducting tissue both in vitro and in vivo and are therefore useful for the prevention and treatment of a wide variety of ventricular and supraventricular arrhythmias including atrial and ventricular fibrillation. Because they do not alter the speed at which impulses are conducted, they have less propensity than current drugs (mostly Class I) to precipitate or aggravate arrhythmias, and also produce less neurological side effects. Some of the compounds also have some positive inotropic activity and therefore are particularly beneficial in patients with impaired cardiac pump function.

Thus the invention provides the compounds of the formula:

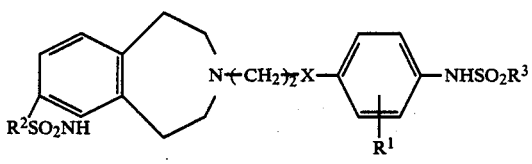
(I)

and their pharmaceutically acceptable salts, wherein
$R^1$ is H, $C_1$–$C_4$ alkyl or $C_1$–$C_4$ alkoxy;
X is O,

or a direct link; and
$R^2$ and $R^3$, which are the same or different, are each $C_1$–$C_4$ alkyl, with the proviso that when X is —NHCO—, $R^2$ and $R^3$ are the same.

These compounds of the formula (I) are antiarrhythmic agents.

The preferred alkyl and alkoxy groups are methyl and methoxy.

$R^1$ is preferably H, methyl or methoxy. $R^1$ is most preferably H. $R^2$ and $R^3$ are preferably the same and are also preferably methyl. X is preferably O or a direct link.

Most preferably, $R^1$ is H, $R^2$ and $R^3$ are methyl, and X is O or a direct link.

The preferred individual compound has the formula:

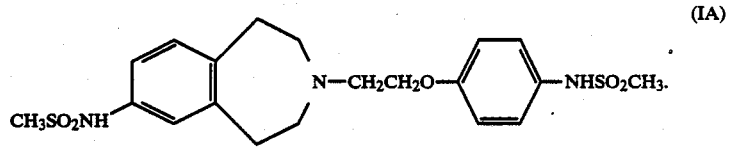
(IA)

The compounds will be named as derivatives of:

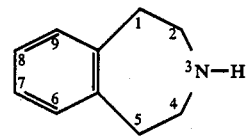

which is 1,2,4,5-tetrahydro-3H-3-benzazepine.

In addition, the invention includes the intermediates of the formula:

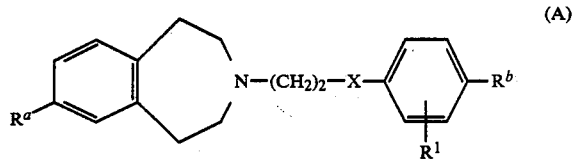
(A)

wherein $R^1$ is as defined for formula (I) and either (a) X is as defined for formula (I) and $R^a$ and $R^b$, which are the same, are —$NO_2$ or —$NH_2$ or (b) X is O or a direct link, $R^a$ is —$NO_2$ and $R^b$ is —$NH_2$.

Also within the scope of the invention are the intermediates of the formulae:

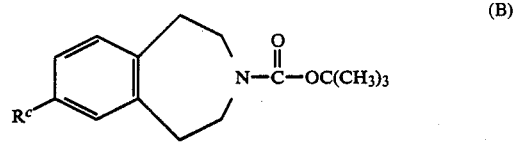
(B)

where $R^c$ is —$NO_2$, —$NH_2$ or —$NHSO_2$ ($C_1$–$C_4$ alkyl); and

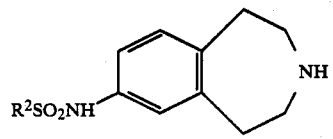
(C)

where $R^2$ is as defined for formula (I).

The compounds of the formula (I) in which $R^2$ and $R^3$ are the same can be prepared by the acylation of the corresponding di-amino compounds according to the following reaction sequence:

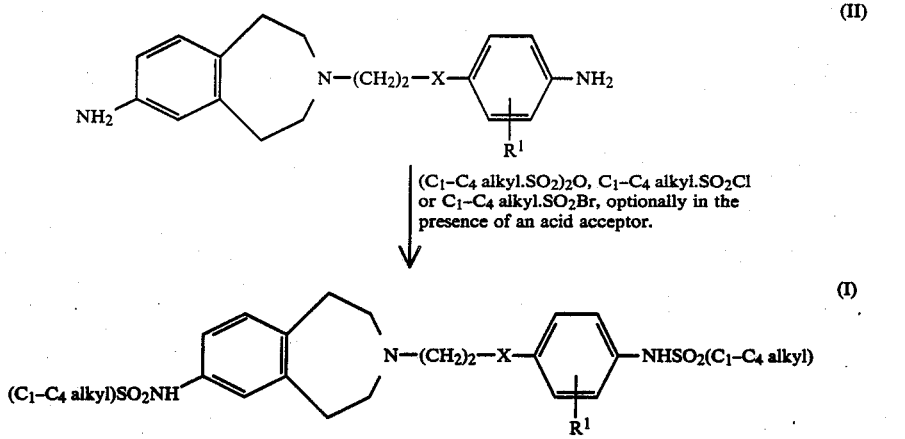

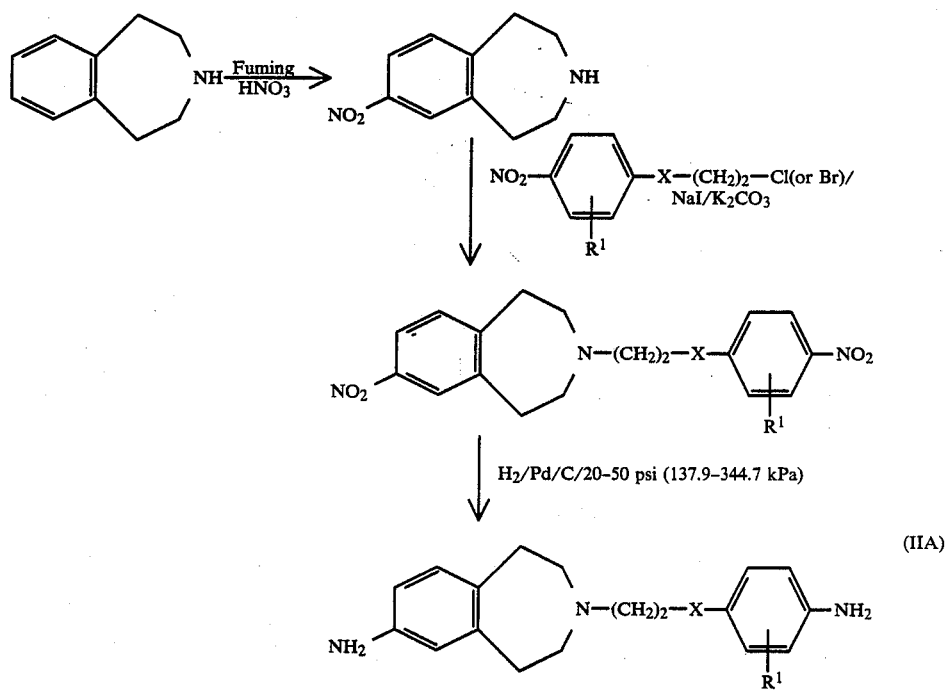

The acylation is typically carried out in a suitable organic solvent, e.g. methylene chloride, pyridine or N-methylmorpholine, at about room temperature and optionally in the presence of an acid acceptor such as triethylamine, potassium carbonate, sodium bicarbonate, pyridine or N-methylmorpholine. It is in fact preferred to carry out the acylation using a $C_1$–$C_4$ alkanesulphonic anhydride or sulphonyl chloride in pyridine or N-methylmorpholine as these function both as the solvent and the acid acceptor. Clearly at least two equivalents of the acylating agent must be used. The product of the formula (I) can then be separated and purified conventionally.

The starting materials of the formula (II) can be prepared by conventional methods as are illustrated in detail in the following Preparations. These routes can be illustrated schematically as follows:

(a) The starting materials of the formula (II) in which X is O or a direct link can be prepared by the following route:

In the above, $R^1$ is as defined for formula (I) and X is O or a direct link.

In the second stage of the above reaction scheme, the use of the sodium iodide catalyst is preferred but not essential. Other leaving groups than halogen, e.g. methanesulphonyloxy, benzenesulphonyloxy or toluenesulphonyloxy, can also be used. The presence of an acid acceptor such as potassium carbonate is preferred. Other acid acceptors such as sodium carbonate or bicarbonate can also be used.

(b) The starting materials of the formula (II) in which X is O or a direct link can also be prepared via the following route:

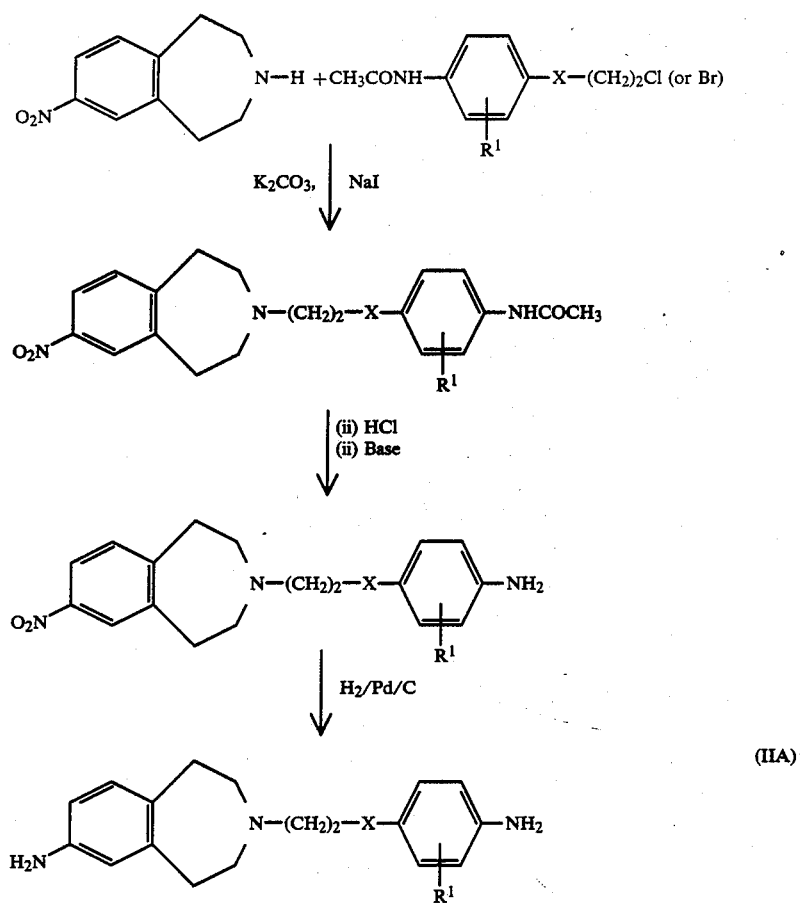
In the above, $R^1$ is as defined for formula (I) and X is O or a direct link.
(c) The starting materials of the formula (II) in which X is —NHCO— can be prepared by the following route:
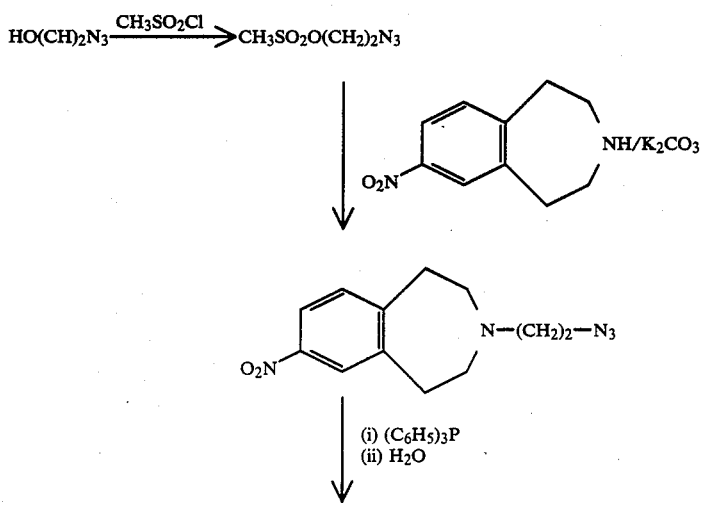

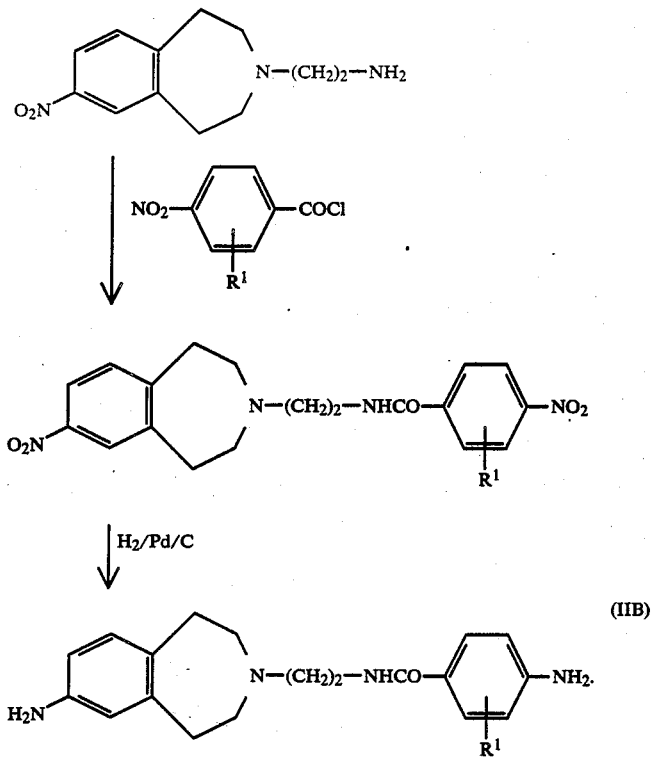

In the above, $R^1$ is as defined for formula (I).

The compounds of the formula (I) in which X is O or a direct link and $R^2$ and $R^3$ are the same or different can be prepared via the following general scheme:

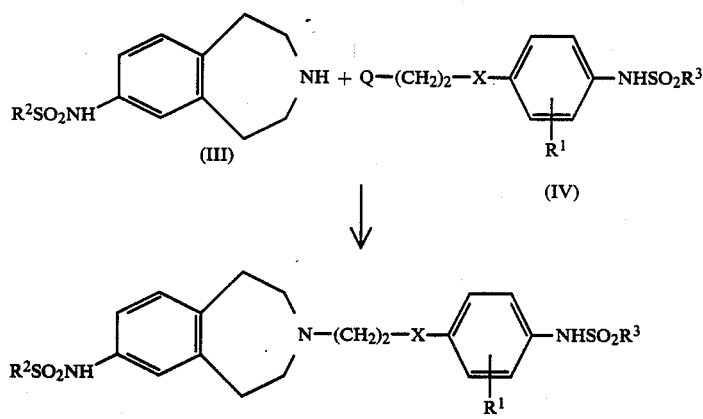

Clearly this method can be used to prepare compounds of the formula (I) in which the alkanesulphonamido groups are the same or different.

In the above, $R^1$, $R^2$, $R^3$ are as defined for formula (I), X is O or a direct link, and Q is a leaving group. Typical leaving groups include chloro, bromo, iodo, methanesulphonyloxy, benzenesulphonyloxy and toluenesulphonyloxy.

The reaction is typically carried out in the presence of an acid acceptor such as triethylamine, sodium or potassium bicarbonate or carbonate in a suitable organic solvent, e.g. ethanol, methanol or acetonitrile, at up to the reflux temperature. The product can then be isolated and purified by conventional means.

The preparation of 7-methanesulphonamido-1,2,4,5-tetrahydro-3H-3-benzazepine is described in Preparations 1 and 18 to 21. The higher alkanesulphonamido derivatives (III) can be prepared analogously using the appropriate alkanesulphonyl chloride in the penultimate step. The starting materials (IV) are either known compounds (see e.g. EP-A-0245997) or can be prepared by conventional techniques as will be known to those skilled in the art.

The pharmaceutically acceptable salts of the compounds of the formula (I) include acid addition salts formed from acids which form non-toxic acid addition salts containing pharmaceutically acceptable anions, such as hydrochloride, hydrobromide, hydroiodide, sulphate or bisulphate, phosphate or hydrogen phosphate, acetate, maleate, fumarate, lactate, tartrate, citrate, gluconate, benzoate, methanesulphonate, besylate and p-toluenesulphonate salts. The compounds also form metal salts, preferred examples of which are the alkaline earth and alkali metal salts. The sodium and potassium salts are most preferred. The salts are preparable by conventional techniques.

For assessment of effects of the compounds on atrial refractoriness, guinea pig right hemiatria are mounted in a bath containing physiological salt solution, and one end is connected to a force transducer. Tissues are stimulated at 1 Hz using field electrodes. Effective refractory period (ERP) is measured by introducing premature stimuli ($S_2$) after every 8th basic stimulus ($S_1$). The $S_1S_2$ coupling interval is gradually increased until $S_2$ reproducibly elicits a propagated response. This is defined as the ERP. The concentration of compound required to increase ERP by 25% ($ED_{25}$) is then determined. ERP is also measured in guinea pig right papillary muscles incubated in physiological salt solution. Muscles are stimulated at one end using bipolar electrodes and the propagated electrogram is recorded at the opposite end via a unipolar surface electrode. ERP is determined as above using the extrastimulus technique. Conduction time is obtained from a digital storage oscilloscope by using the interval between the stimulus artefact and the peak of the electrogram (i.e. the time required for the impulse to travel along the length of the muscle).

Atrial and ventricular ERP's are also measured in anaesthetised or conscious dogs by the extrastimulus technique whilst the atrium or right ventricle is being paced at a constant rate.

The compounds of the formula (I) can be administered alone but will generally be administered in admixture with a pharmaceutical carrier selected with regard to the intended route of administration and standard pharmaceutical practice. They can be administered both to patients suffering from arrhythmias and also prophylactically to those likely to develop arrhythmias. For example they may be administered orally in the form of tablets containing such excipients as starch or lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic.

For administration to man in the curative or prophylactic treatment of cardiac conditions such as ventricular and supraventricular arrhythmias, including atrial and ventricular fibrillation, it is expected that oral dosages of the compounds of the formula (I) will be in the range from 1 to 75 mg daily, taken in up to 4 divided doses per day, for an average adult patient (70 kg). Dosages for intravenous administration would be expected to be within the range 0.5 to 10 mg per single dose as required. A severe cardiac arrythmia is preferably treated by the i.v. route in order to effect a rapid conversion to the normal rhythm. Thus for a typical adult patient individual tablets or capsules might for example contain 1 to 25 mg of active compound, in a suitable pharmaceutically acceptable vehicle or carrier. Variation may occur depending on the weight and condition of the subject being treated as will be known to medical practitioners.

Thus the present invention provides a pharmaceutical composition comprising a compound of the formula (I) as defined above or a pharmaceutically acceptable salt thereof, together with a pharmaceutically acceptable diluent or carrier.

The invention also provides a method of preventing or reducing cardiac arrhythmias in a human being, which comprises administering to said human an effective amount of a compound of the formula (I) or pharmaceutically acceptable salt thereof, or of a pharmaceutical composition as defined above.

The invention yet further provides a compound of the formula (I) or a pharmaceutically acceptable salt thereof, for use as a medicament, particularly for use as an antiarrhythmic agent.

The invention also provides the use of a compound of the formula (I), or of a pharmaceutically acceptable salt thereof, for the manufacture of a medicament for the prevention or reduction of cardiac arrhythmias.

The following Examples, in which all temperatures are in ° C., illustrate the preparation of the compounds of the formula (I):

EXAMPLE 1

7-Methanesulphonamido-3-(2-[4-methanesulphonamidophenoxy]ethyl)-1,2,4,5-tetrahydro-3H-3-benzazepine, free base and hydrochloride Method (A) (Free Base)

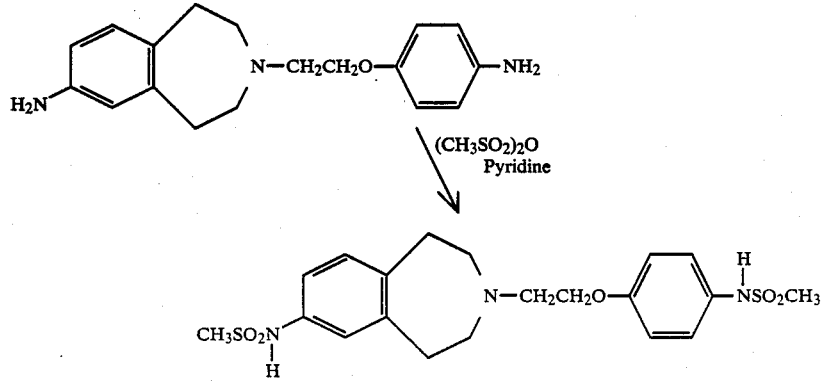

Methanesulphonic anhydride (0.2) was added to a solution of 7-amino-3-(2-[4-aminophenoxy]ethyl)-

1,2,4,5-tetrahydro-3H-3-benzazepine (0.37 g) in pyridine (30 ml) cooled to 0° and the mixture was then stirred at room temperature for 72 hours. The solvent was evaporated in vacuo and the residue taken up in methylene chloride, washed three times with aqueous sodium bicarbonate and three times with brine. The organic layer was dried ($Na_2SO_4$), filtered and evaporated in vacuo to give an oil which was purified by column chromatography on silica eluting with methylene chloride containing methanol (0% up to 5%). The product-containing fractions were combined and evaporated to give a semi-solid which was triturated with ether, filtered and dried to give the title compound as an amorphous powder, yield 0.19 g, m.p. indistinct.

Analysis %: Found: C,53.05; H,6.1; N,8.9; Calculated for $C_{20}H_{27}N_3O_5S_2$: C,53.0; H,6.00; N,9.3.

$^1$H-N.m.r. ($CDCl_3$):δ=7.2 (d, 2H); 7.05 (q, 2H); 7.00 (s, 1H); 6.9 (d, 2H); 4.1 (t, 2H); 3.00 (t, 2H); 3.00 (s, 3H); 2.95 (s, 3H); 2.9 (m, 4H); 2.8 (m, 4H).

The above reaction was also repeated using methanesulphonyl chloride and triethylamine in ethanol at room temperature with silimar results.

Method (B) (Hydrochloride)

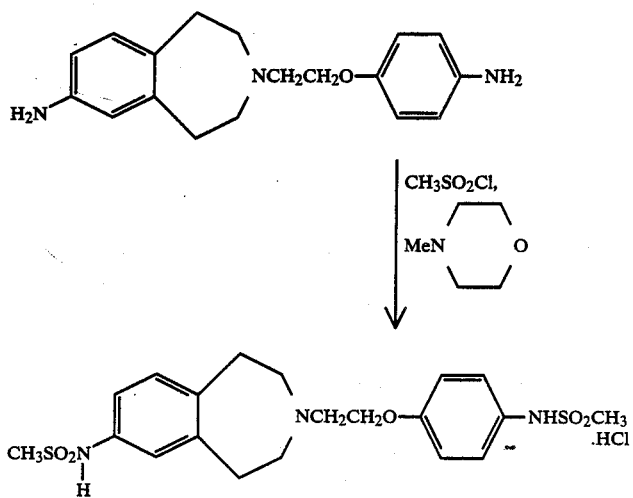

Methanesulphonyl chloride (70.3 g) was added dropwise over 45 minutes to a stirred solution of 7-amino-3-(2-[4-aminophenoxy]-ethyl)-1,2,4,5-tetrahydro-3H-3-benzazepine (83 g) in N-methylmorpholine (700 ml) cooled to 0°. The reaction was allowed to warm to 15° and further methanesulphonyl chloride (14.6 g) was added. The solvent was decanted from the heavy precipitate into water (3000 ml). The aqueous solution was extracted with ethyl acetate (2×500 ml). The precipitate was taken up in the combined organic extracts, washed with water (2×500 ml), dried ($MgSO_4$) and evaporated in vacuo. The resulting oil was taken up in methanol (500 ml) containing 2.5M sodium hydroxide (400 ml) and stirred at 40° for ½ hour. The methanol was evaporated in vacuo and the aqueous layer was washed twice with methylene chloride. The aqueous layer was diluted with water (1000 ml) and adjusted to pH 6.5 with concentrated hydrochloric acid. The resulting precipitate was granulated, filtered, washed with water then dried in vacuo at 60°, yield 110.4 g. The product was recrystallised from industrial methylated spirits (1100 ml) and methanol (1320 ml) to give the title compound, yield 73.5 g, m.p. 221°.

Analysis %: Found: C,48.9; H,5.8; N,8.6; S,13.0; Calculated for $C_{20}H_{27}N_3O_5S_2$. HCl: C,49.0; H,5.8; N,8.6; S,13.1.

EXAMPLE 2

7-Methanesulphonamido-3-(4-methanesulphonamidophenethyl)-1,2,4,5-tetrahydro-3H-3-benzazepine The title compound, m.p. 184°-7°, was prepared similarly to Example 1 Method (A) by the acylation of the corresponding di-amino compound with methanesulphonic anhydride except that the reaction time was 18 hours. The solvate was detected and quantified by $^1$H-n.m.r. spectroscopy.

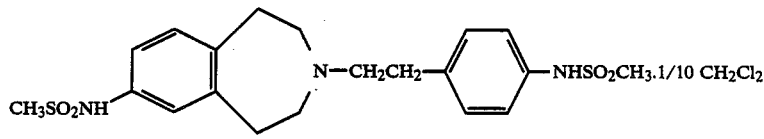

Analysis %: Found: C,53.9; H,6.0; N,9.3; Calculated for $C_{20}H_{27}N_3O_4S_2$. 1/10 $CH_2Cl_2$: C,54.1; H,6.15; N,9.4.

$^1$H-N.m.r. (DMSO $d_6$): δ =9.55 (br s, 2H); 7.1 (q, 4H); 7.05 (d, 1H); 6.95 (s, 1H); 6.90 (d, 1H); 2.95 (s, 6H); 2.8 (br s, 4H); 2.65 (m, 8H).

EXAMPLE 3

7-Methanesulphonamido-3-[2-(4-methanesulphonamido-2-methoxybenzamido)ethyl]-1,2,4,5-tetrahydro-3H-3-benzazepine

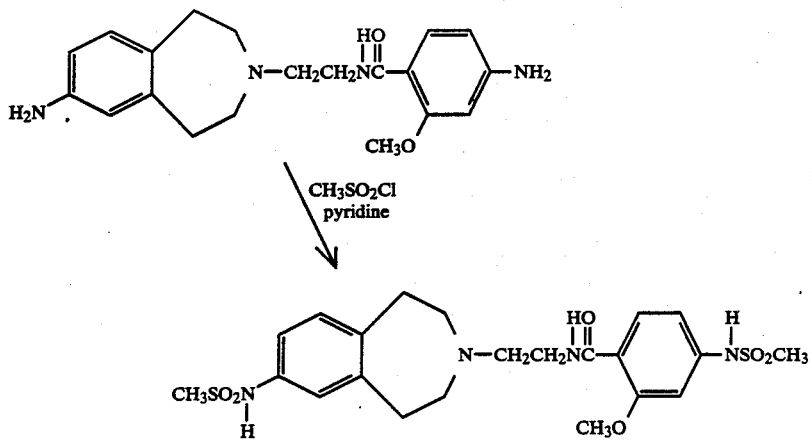

Methanesulphonyl chloride (0.155 ml) was added dropwise to a solution of 7-amino-3-[2-(4-amino-2-methoxybenzamido)ethyl]-1,2,4,5-tetrahydro-3H-3-benzazepine in pyridine cooled to 0°, and the reaction mixture was stirred for a further 18 hours at room temperature. The solvent was evaporated in vacuo and the residue taken up in methylene chloride, washed three times with aqueous sodium bicarbonate and three times with brine. The organic layer was dried ($Na_2SO_4$), filtered and evaporated to give an oil, in which thin layer chromatography detected the presence of some unreacted starting material. The oil was therefore taken up in pyridine and treated with methanesulphonyl chloride (0.05 ml), and the reaction mixture was stirred at room temperature for 72 hours. The solvent was then evaporated in vacuo and the residue taken up in methylene chloride, washed three times with aqueous sodium bicarbonate and three times with brine. The organic layer was dried ($Na_2SO_4$), filtered and evaporated to give an oil. The resulting oil was then purified by column chromatography on silica eluting with methylene chloride containing methanol (0% up to 5%) and the product-containing fractions were combined and evaporated in vacuo to give the title compound as a colourless foam, yield 0.32 g.

Analysis %: Found: C,51.7; H,6.0; N,10.6; Calculated for $C_{22}H_{30}N_4O_6S_2$. C,51.7; H,5.9; N,11.0.

$^1$H-N.m.r. ($CDCl_3$)$\delta$=8.4 (br s, 1H); 8.25 (d, 1H); 7.1 (d,1H); 7.05 (s, 2H); 7.0 (d, 1H); 6.8 (d, 1H); 4.0 (s, 3H); 3.6 (m, 2H); 3.1 (s, 3H); 3.05 (s, 3H); 2.95 (br s, 4H); 2.7 (br s, 6H).

EXAMPLE 4

7-Methanesulphonamido-3-[2-(4-methanesulphonamido-3-methylphenoxy)ethyl]-1,2,4,5-tetrahydro-3H-3-benzazepine

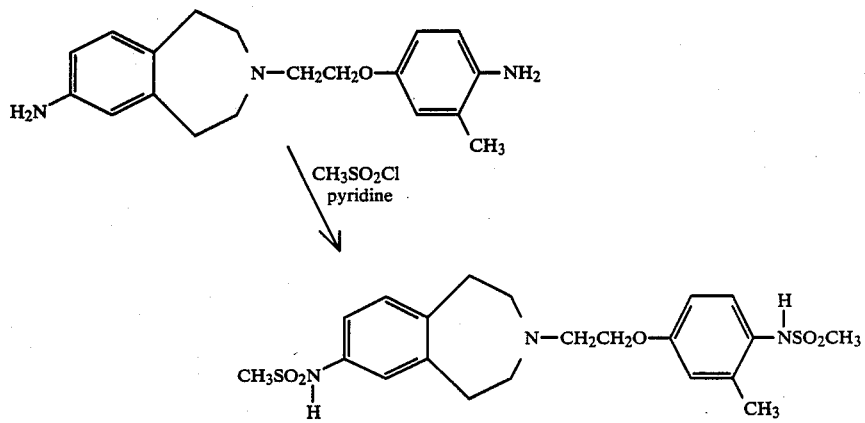

Methanesulphonyl chloride (0.18 ml) was added dropwise to a solution of 7-amino-3-[2-(4-amino-3-methylphenoxy)ethyl]-1,2,4,5-tetrahydro-3H-3-benzazepine (0.36 g) in pyridine (30 ml) cooled to 0°, and the mixture was then stirred at room temperature for 72 hours. The solvent was evaporated in vacuo and the residue was taken up in methylene chloride and washed three times with saturated aqueous sodium bicarbonate and three times with brine. The organic layer was dried ($Na_2SO_4$), filtered and evaporated in vacuo to give an oil which was triturated with methylene chloride to give a solid. Recrystallisation of the solid from ethanol/ethyl acetate gave the title compound, yield 0.28 g, m.p. 173°–174°.

Analysis %: Found: C,54.3; H,6.3; N,8.7; Calculated for $C_{21}H_{29}N_3O_5S_2$: C,53.9; H,6.25; N,9.0.

$^1$H-N.m.r. (DMSO d$_6$): δ =7.15 (d, 1H); 7.05 (d, 1H); 6.95 (s, 1H); 6.90 (d, 1H); 6.85 (d, 1H); 6.75 (dd, 1H); 4.05 (t, 2H); 2.95 (s, 3H); 2.90 (s, 3H); 2.85 (t, 2H); 2.8 (br s, 4H); 2.7 (br s, 4H); 2.3 (s, 3H).

EXAMPLE 5

Preparation of
7-methanesulphonamido-3-(4-methanesulphonamidophenethyl)-1,2,4,5-tetrahydro-3H-3-benzazepine

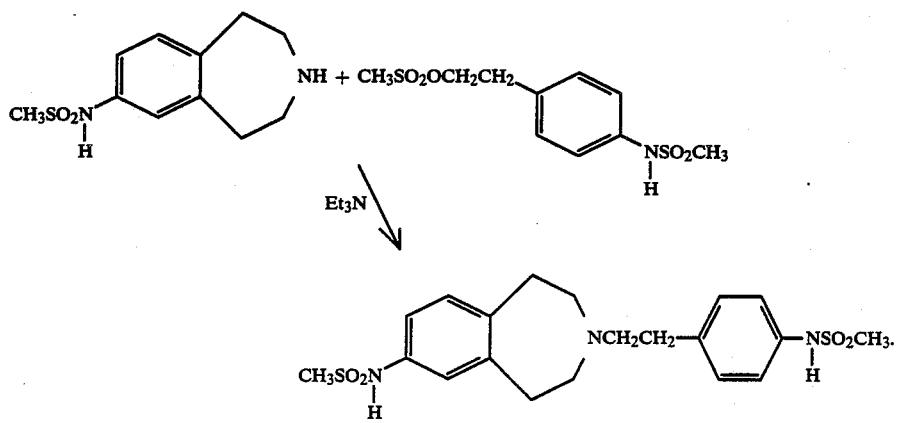

7-Methanesulphonamido-1,2,4,5-tetrahydro-3H-3-benzazepine (0.21 g), 4-[2-(methanesulphonyloxy)ethyl]methanesulphonanilide (0.26 g) (see EP-A-0245997, Preparation 7) and triethylamine (0.12 ml) were heated at reflux temperature in ethanol for 24 hours. The solvent was removed in vacuo and the residue taken up in methylene chloride, washed with aqueous sodium bicarbonate, brine and then water. The organic layer was dried (Na$_2$SO$_4$), evaporated in vacuo and the residue purified by column chromatography on silica eluting with methylene chloride containing methanol (0% up to 5%). The product-containing fractions were combined and evaporated to give a solid which was recrystallised to give the title compound, yield 0.05 g, m.p. 190°–193°.

Analysis %: Found: C,55.1; H,6.3; N,9.4; Calculated for C$_{20}$H$_{27}$N$_3$O$_4$S$_2$: C,54.9; H,6.2; N,9.6.

The following Preparations illustrate the preparation of certain of the starting materials used in the previous Examples. All temperatures are in °C:

Preparation 1

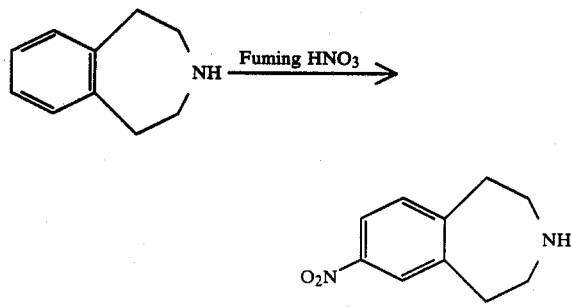

(see also J. Het. Chem., p. 779, vol. 8, 1971)

7-Nitro-1,2,4,5-tetrahydro-3H-3-benzazepine 1,2,4,5-Tetrahydro-3H-3-benzazepine (1 g) (see P. Ruggli et al., Helv. Chem. Acta, 18, 1388 [1935]) was added slowly, dropwise to stirred fuming nitric acid (25 ml. density 1.5 gm/ml) cooled to −10°. Stirring was continued at −10° for 1 hour, and the reaction mixture was then poured onto ice, the precipitate collected by filtration and dried to give the title compound as the nitrate salt, yield 1.4 g. A sample was recrystallised from water, m.p. 203°–204°.

Analysis %: Found: C,46.9; H,5.4; N,16.6; Calculated for C$_{10}$H$_{12}$N$_2$O$_2$.HNO$_3$: C,47.05; H,5.1; N,16.5.

The bulk of the nitrate salt was suspended in water, chilled and neutralised with 5M sodium hydroxide and the precipitate collected by filtration, recrystallised from water and dried to give the title compound, yield 0.6 g, m.p. 53°–56°.

Analysis %: Found: C,62.9; H,6.45; N,14.8; Calculated for C$_{10}$H$_{12}$N$_2$O$_2$: C,62.5; H,6.3; N,14.6.

Preparation 2

7-Nitro-3-(2-[4-nitrophenoxy]ethyl)-1,2,4,5-tetrahydro-3H-3-benzazepine

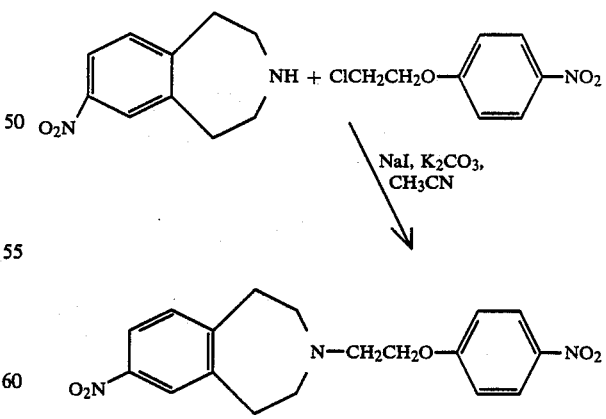

7-Nitro-1,2,4,5-tetrahydro-3H-3-benzazepine (0.7 g), 2-[4-nitrophenoxy]ethyl chloride (0.73 g) (see C. A. [1955], 49, 3163e), sodium iodide (0.5 g) and potassium carbonate in acetonitrile (50 ml) were heated under reflux for 3 days. After cooling, the solvent was removed in vacuo, the residue dissolved in ethyl acetate and washed once with water, once with sodium carbonate and twice with brine. The organic layer was dried (Na$_2$SO$_4$) and evaporated in vacuo to give an oil which was purified by column chromatography on silica eluting with methylene chloride containing methanol (0% up to 1%). The product-containing fractions were combined and evaporated in vacuo to give the product as an orange oil, yield 1.0 g.

Analysis %: Found: C,60.5; H,5.5; N,11.9; Calculated for C$_{18}$H$_{19}$N$_3$O$_5$: C,60.5; H,5.4; N,11.8.

Preparation 3

7-Nitro-3-(4-nitrophenethyl)-1,2,4,5-tetrahydro-3H-3-benzazepine hemihydrate

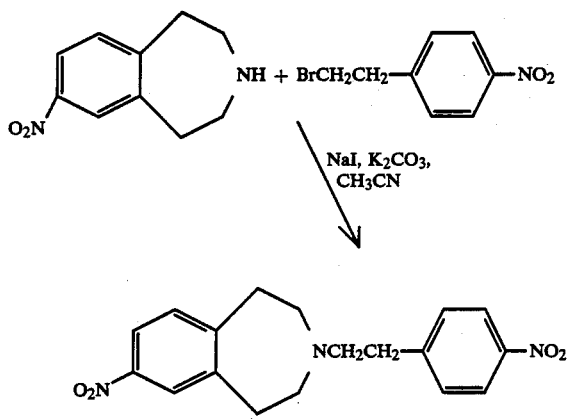

The title compound was prepared similarly to Preparation 2 by the reaction of 7-nitro-1,2,4,5-tetrahydro-3H-3-benzazepine (0.5 g) and 4-nitrophenethyl bromide (0.6 g), which, after 18 hours reflux, gave the title compound as an oil, yield 0.29 g.

Analysis %: Found: C,61,7; H,5.5; N,12.1; Calculated for C$_{18}$H$_{19}$N$_3$O$_4$·½H$_2$O:C,61.7; H,5.75; N,12.0.

Preparation 4

7-Amino-3-(2-[4-aminophenoxy]ethyl)-1,2,4,5-tetrahydro-3H-3-benzazepine

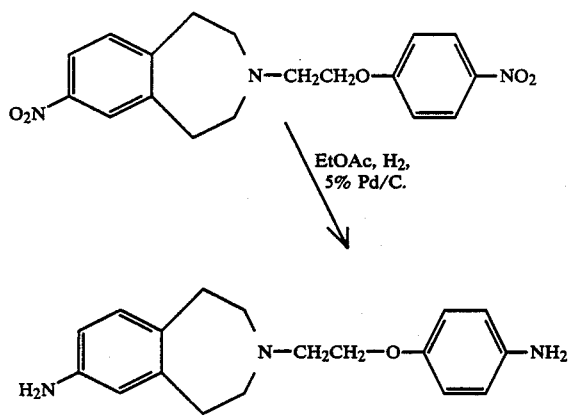

7-Nitro-3-(2-[4-nitrophenoxy]ethyl)-1,2,4,5-tetrahydro-3H-3-benzazepine (0.42 g) was stirred at room temperature under a hydrogen atmosphere [344.7 kPa (50 p.s.i.)] in ethyl acetate containing 5% Pd/C for 4 hours. The catalyst was then removed by filtration and the filtration evaporated in vacuo to give the title compound as an oil, which was used directly without further purification, yield 0.3 g.

$^1$H-N.m.r. (CDCl$_3$):δ=6.9 (d, 1H); 6.7 (q, 4H); 6.45 (q, 2H); 4.05 (t, 2H); 2.95 (t, 2H); 2.80 (m, 8H).

Preparation 5

7-Amino-3-(4-aminophenethyl)-1,2,4,5-tetrahydro-3H-3-benzazepine

The title compound was prepared similarly to Preparation 4 by the hydrogenation of the corresponding di-nitro compound.

$^1$H-N.m.r. (CDCl$_3$);δ=7.02 (d, 2H); 6.9 (d, 1H); 6.65 (d, 2H); 6.5 (s, 1H); 6.45 (d, 1H); 2.9 (br s, 4H); 2.7 (br s, 8H).

Preparation 6

2-Methanesulphonyloxyethyl azide

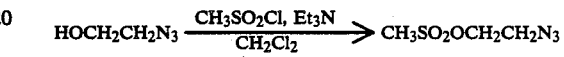

A solution of methanesulphonyl chloride (5.7 g) in methylene chloride (20 ml) was added dropwise to a stirred solution of 2-azidoethanol (4.3 g) and triethylamine (5.0 g) in methylene chloride (80 ml). After 2 hours stirring at room temperature the reaction mixture was washed with water, dried (MgSO$_4$) and evaporated to dryness in vacuo to give the title compound as a yellow oil, yield 7 g, which was used directly without further purification.

$^1$H-N.m.r. (CDCl$_3$):δ=4.25 (t, 2H); 3.5 (t, 2H); 3.0 (s, 3H).

Preparation 7

3-(2-Azidoethyl)-7-nitro-1,2,4,5-tetrahydro-3H-3-benzazepine

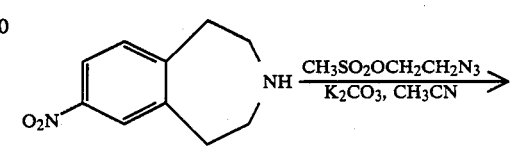

7-Nitro-1,2,4,5-tetrahydro-3H-3-benzazepine (1.1 g), 2-methanesulphonyloxyethyl azide (0.92 g) and potassium carbonate (0.76 g) were heated under reflux in acetonitrile for 18 hours. The solvent was evaporated in vacuo and the residue taken up in ethyl acetate then washed three times with aqueous sodium carbonate and three times with brine. The organic layer was dried, filtered and evaporated in vacuo to give an oil which was purified by chromatography on silica eluting with ethyl acetate/hexane (1:1). The product-containing fractions were combined and evaporated to give the title compound as an oil, yield 0.65 g, which was used without further purification.

I.R. ν=2100 cm$^{-1}$ (azide).

$^1$H-N.m.r. (CDCl$_3$):δ=8.05 (d, 1H); 8.05 (s, 1H); 7.3 (d, 1H); 3.4 (t, 2H); 3.1 (m, 4H); 2.75 (m, 6H).

Preparation 8

3-(2-Aminoethyl)-7-nitro-1,2,4,5-tetrahydro-3H-3-benzazepine

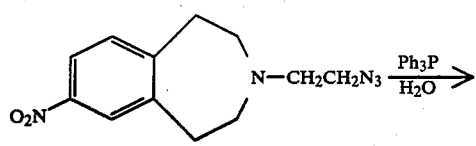

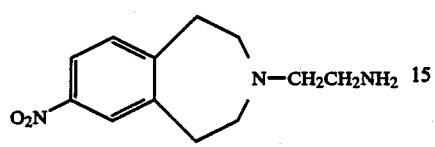

Triphenylphosphine (0.71 g) was added to a solution of 3-(2-azidoethyl)-7-nitro-1,2,4,5-tetrahydro-3H-3-benzazepine (0.68 g) in dry tetrahydrofuran under a nitrogen atmosphere and the reaction mixture was then stirred at room temperature for 18 hours and heated at 50° for 5 hours. After cooling, water was added and the mixture was stirred at room temperature for 3 days. The solvent was then evaporated in vacuo and the residue was diluted with 2M hydrochloric acid and washed three times with ethyl acetate. The aqueous layer was made alkaline (pH=12) with 5M sodium hydroxide and extracted three times with ethyl acetate. The latter organic extracts were combined and dried (Na₂SO₄), filtered and evaporated in vacuo to give the title compound as an oil, yield 0.56 g, which was used without further purification.

Preparation 9

7-Nitro-3-(2-[2-methoxy-4-nitrobenzamido]ethyl-1,2,4,5-tetrahydro-3H-3-benzazepine

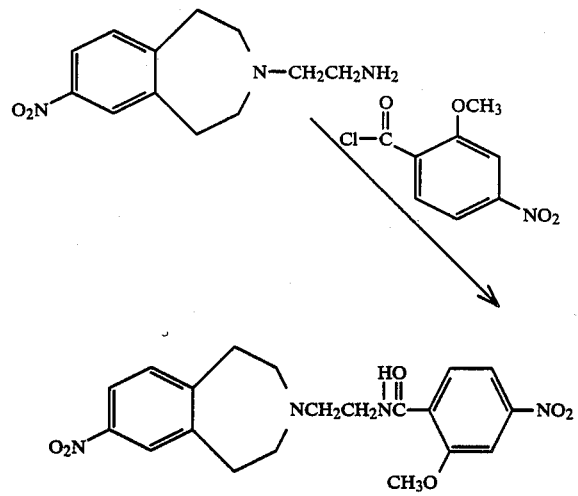

A solution of 2-methoxy-4-nitrobenzoyl chloride (0.56 g) in methylene chloride was added dropwise to a stirred solution of 3-(2-aminoethyl)-7-nitro-1,2,4,5-tetrahydro-3H-3-benzazepine (0.56 g) in methylene chloride cooled to 0°, and stirring was continued at room temperature for 1 hour. The solvent was then evaporated in vacuo, the residue triturated with ether, and filtered. The precipitate was suspended in aqueous sodium carbonate and extracted three times with methylene chloride. The organic layers were combined and then washed three times with brine, dried (Na₂SO₄), filtered and evaporated in vacuo. The residue was purified by column chromatography on silica eluting with methylene chloride containing methanol (0% up to 2%). The product-containing fractions were combined and evaporated in vacuo to give the title compound, yield 0.55 g, m.p. 138°–140°.

Analysis %: Found: C,58.05; H,5.5; N,13.1; Calculated for C₂₀H₂₂N₄O₆: C,58.0; H,5.35; N,13.5.

Preparation 10

7-Amino-3-(2-[4-amino-2-methoxybenzamido]ethyl)-1,2,4,5-tetrahydro-3H-3-benzazepine

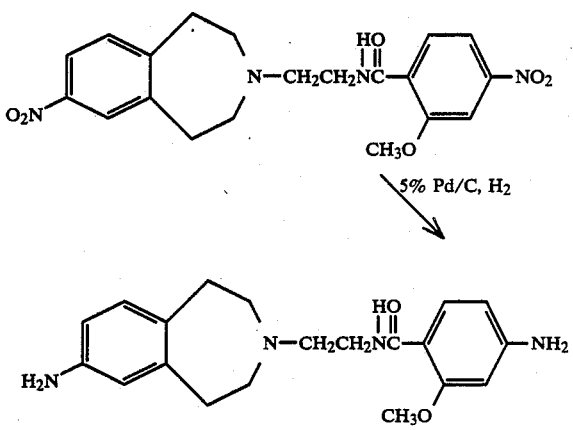

7-Nitro-3-(2-[2-methoxy-4-nitrobenzamido]ethyl)-1,2,4,5-tetrahydro-3H-3-benzazepine (0.52 g) was stirred under a hydrogen atmosphere [344.7 kPa (50 p.s.i.)] in an ethanol/methanol (1:1) solution at room temperature for 3 hours. The catalyst was then removed by filtration and the filtrate evaporated in vacuo to give the title compound as a foam, yield 0.42 g, which was used directly without further purification.

¹H-N.m.r. (CDCl₃):δ=8.4 (br, s, 1H); 8.1 (d, 1H); 6.95 (d, 1H); 6.5 (s, 2H); 6.45 (d, 1H); 6.35 (q, 1H); 6.25 (d, 1H); 4.0 (s, 2H); 3.95 (s, 3H); 3.6 (s, 2H); 2.9 (m, 4H); 2.7 (m, 2H).

Preparation 11

2-Methoxy-4-nitrobenzoyl chloride

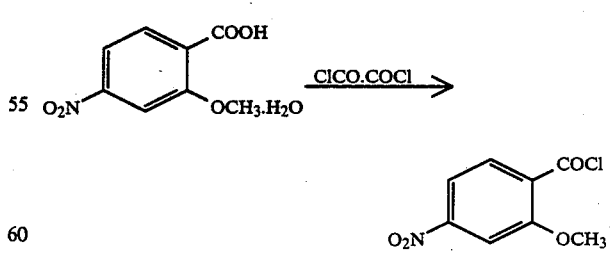

(J. Chem. Soc., 1917,111, 220.)

Oxalyl chloride (0.81 ml) in methylene chloride (10 ml) was added dropwise to a solution of 2-methoxy-4-nitrobenzoic acid monohydrate (1 g) in methylene chloride (40 ml) and dimethylformamide (1 drop) and the reaction mixture was stirred at room temperature for 1 hour after gas evolution ceased. The solvent was then evaporated in vacuo to give an oil which was crystallised from cold ethyl acetate/hexane to give the title compound, yield 0.7 g.

This low melting compound was used directly without further purification.

Preparation 12

2-(4-Nitrophenoxy)ethyl chloride

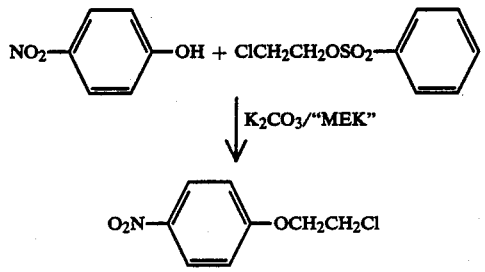

A mixture of 4-nitrophenol (139 g, 1 mole), 2-(benzenesulphonyloxy)ethyl chloride (220.5 g, 1 mole—see Ber. (1920), 53, 1836) and anhydrous potassium carbonate (138 g, 1 mole) in methyl ethyl ketone ("MEK'-'—1000 ml) was stirred at reflux for 16 hours. After cooling, the mixture was poured onto water and the organic layer was separated. Following two further extractions with methyl ethyl ketone, the combined organic fractions were dried (MgSO4), filtered and evaporated. The resultant solid was crystallised from ethanol to give the title compound, (165.8 g), m.p. 60°.

Analysis %: Found: C,47.65; H,4.0; N,7.0; Calculated for $C_8H_8ClNO_3$: C,47.7; H,4.0; N,7.0.

Preparation 13

4-(2-Chloroethoxy)-2-methylacetanilide

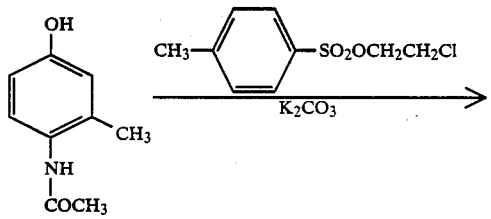

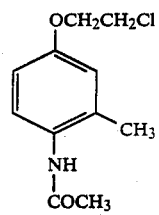

Annalen, 259, 217 (1890).

A mixture of 4-hydroxy-2-methylacetanilide (33 g), 2-toluenesulphonyloxyethyl chloride (46.9 g) and potassium carbonate (23.6) were heated under reflux in butan-2-one (200 ml) for 6 hours. The reaction mixture was then cooled, diluted with water and the precipitate collected by filtration, washed with water and recrystallised from ethanol to give the title compound, yield 22 g, m.p. 127°–129°.

Analysis %: Found: C,58.0; H,6.2; N,6.15; Calculated for $C_{11}H_{14}ClNO_2$: C,58.2; H,6.3; N,6.4.

Preparation 14

3-[2-(4-Acetylamino-3-methylphenoxy)ethyl]-7-nitro-1,2,4,5-tetrahydro-3H-3-benzazepine

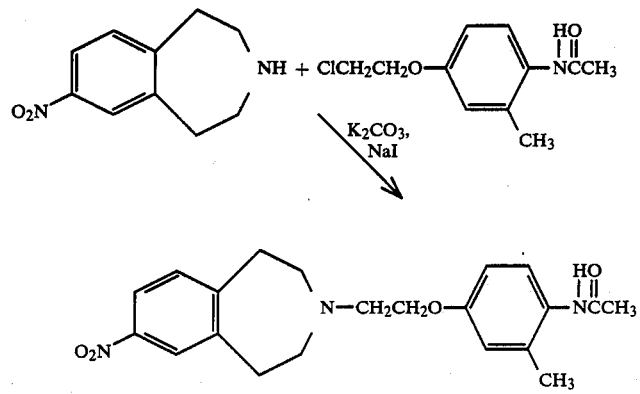

7-Nitro-1,2,4,5-tetrahydro-3H-3-benzazepine (1.69 g), 2-methyl-4-(2-chloroethoxy)acetanilide (2 g), potassium carbonate (1.21 g) and sodium iodide (1.32 g) were heated at reflux in acetonitrile for 5 days. After cooling the solvent was removed in vacuo and the residue was diluted with sodium carbonate solution and extracted three times with methylene chloride. The combined organic extracts were washed three times with brine, dried (Na2SO4) and evaporated to give a semi-solid which was triturated with ether to give a solid. Recrystallisation of the solid from ethyl acetate/hexane gave the title compound, yield 1.6 g, m.p. 132°–134°.

Analysis %: Found: C,65.9; H,6.7; N,11.0; Calculated for $C_{21}H_{25}N_3O_4$: C,65.8; H,6.6; N,11.0.

Preparation 15

3-[2-(4-Amino-3-methylphenoxy)ethyl]-7-nitro-1,2,4,5-tetrahydro-3H-3-benzazepine dihydrochloride

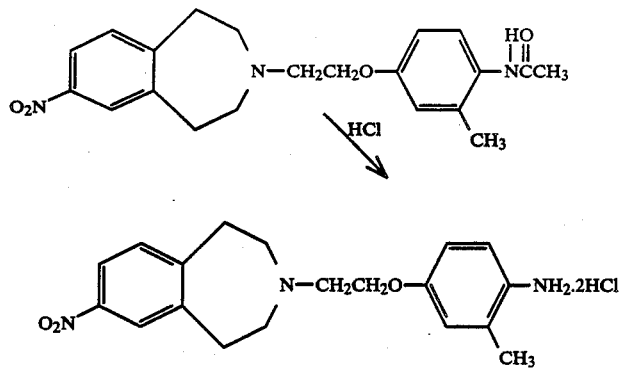

3-[2-(4-Acetylamino-3-methylphenoxy)ethyl]-7-nitro-1,2,4,5-tetrahydro-3H-3-benzazepine (1 g) was stirred in 6M hydrochloric acid (20 ml) at 90° for 18 hours. After cooling, the precipitate was collected by filtration and recrystallised from ethanol to give the title compound, yield 0.65 g, m.p. 253°–256°.

Analysis %: Found: C,53.9; H,6.6; N,9.1; Calculated for $C_{19}H_{23}N_3O_2.2HCl.\frac{1}{2}H_2O.\frac{1}{4}C_2H_5OH$*: C,53.8; H,6.3; N,9.4.

*¼ Mole of ethanol in the sample was detected and quantified by $^1$H-n.m.r.

$^1$H-n.m.r. (CDCl$_3$)δ=8.0 (s, 1H); 8.0 (d, 1H); 7.5 (d, 1H); 7.3 (d, 1H); 6.9 (s, 1H); 6.9 (q, 2H); 4.1 (t, 2H); 3.05 (m, 6H); 2.8 (br s, 4H); 2.25 (s, 3H); 2.2 (s, 3H).

Preparation 16

3-[2-(4-Amino-3-methylphenoxy)ethyl]-7-nitro-1,2,4,5-tetrahydro-3H-3-benzazepine

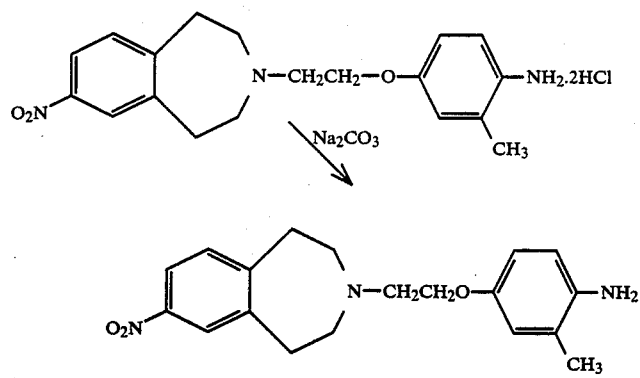

3-[2-(4-Amino-3-methylphenoxy)ethyl]-7-nitro-1,2,4,5-tetrahydro-3H-3-benzazepine dihydrochloride hemihydrate (0.62 g) was dissolved in saturated aqueous sodium carbonate (20 ml) and extracted three times with ethyl acetate (30 ml). The combined organic extracts were dried (Na$_2$SO$_4$) and evaporated in vacuo to give the title compound as an oil, yield 0.5 g, which was used directly without further purification.

Preparation 17

7-Amino-3-[2-(4-amino-3-methylphenoxy)ethyl]-1,2,4,5-tetrahydro-3H-3-benzazepine

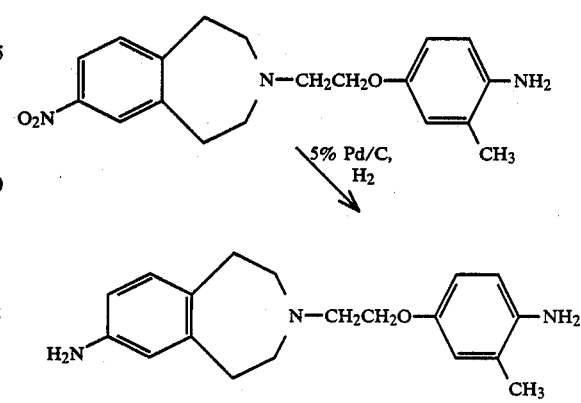

3-[2-(4-Amino-3-methylphenoxy)ethyl]-7-nitro-1,2,4,5-tetrahydro-3H-3-benzazepine (0.5 g) was stirred at room temperature under a hydrogen atmosphere [344.7 kPa (50 p.s.i.)]in ethyl acetate (20 ml) and methanol (20 ml) containing 5% Pd/C (0.075 g) for 3 hours. The catalyst was then removed by filtration and the filtrate was evaporated in vacuo to give the title compound as an oil, yield 0.385 g, which was used directly without further purification.

$^1$H-N.m.r. (CDCl$_3$):δ=6.9 (d, 1H); 6.7 (s, 1H); 6.6 (s, 2H); 6.5 (s, 2H); 4.05 (t, 2H); 2.95 (t, 2H); 2.8 (m, 8H); 2.2 (s, 3H).

Preparation 18

3-Tertiary-butoxycarbonyl-7-nitro-1,2,4,5-tetrahydro-3H-3-benzazepine

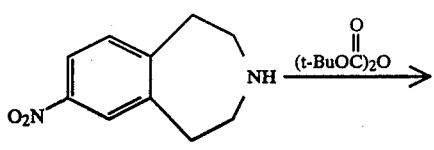

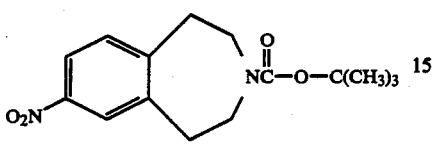

A solution of di-t-butyldicarbonate (2.18 g) in dry methylene chloride (15 ml) was added dropwise to a stirred solution of 7-nitro-1,2,4,5-tetrahydro-3H-3-benzazepine (1.92 g) in dry methylene chloride (40 ml) cooled to 0°. After stirring for 18 hours at room temperature the solvent was removed in vacuo to give an oil which was dissolved in methylene chloride, then washed twice with aqueous sodium bicarbonate, three times with 1M hydrochloric acid and finally twice with brine. The methylene chloride solution was dried (Na$_2$SO$_4$) and evaporated in vacuo to give an oil which was triturated with hexane to give the title compound, yield 2.33 g, m.p. 106–108.

Analysis %: Found: C,61.7; H,7.0; N,9.6; Calculated for C$_{15}$H$_{20}$N$_2$O$_4$: C,61.6; H,6.9; N,9.6.

Preparation 19

7-Amino-3-tertiary-butoxycarbonyl-1,2,4,5-tetrahydro-3H-3-benzazepine

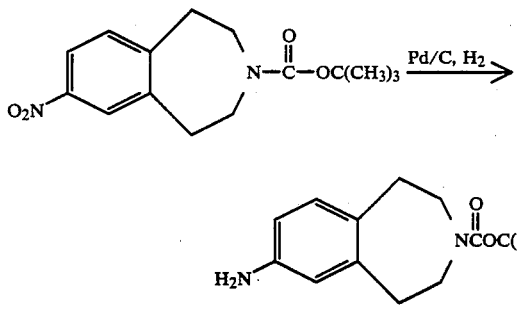

A solution of 3-tertiary-butoxycarbonyl-7-nitro-1,2,4,5-tetrahydro-3H-3-benzazepine (2.1 g) was stirred under a hydrogen atmosphere (50 p.s.i. equivalent to 344.7 kPa) in ethanol (20 ml) and methanol (20 ml) solution containing 5% Pd/C (0.21 g) for 3 hours. The catalyst was removed by filtration and the solvent evaporated to give the title compound as an oil, yield 2.0 g.

A sample (100 mg) of this oil was chromatographed on silica eluting with methylene chloride containing methanol (0% up to 2%). The product-containing fractions were combined and evaporated in vacuo to give the title compound as a low melting solid (~30°), yield 58 mg.

Analysis %: Found: C,69.0; H,8.6; N,10.3; Calculated for C$_{15}$H$_{22}$N$_2$O$_2$: C,68.7; H,8.45; N,10.7.

Preparation 20

7-Methanesulphonamido-3-tertiary-butoxycarbonyl-1,2,4,5-tetrahydro-3H-3-benzazepine

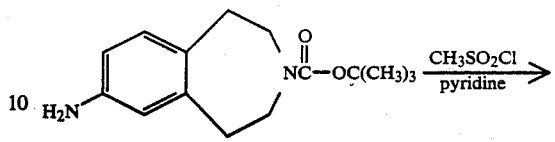

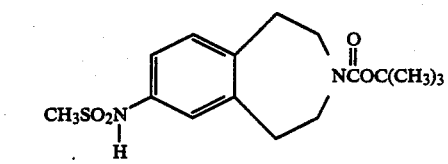

Methanesulphonyl chloride (0.56 ml) was added dropwise to a solution of 7-amino-3-tertiary-butoxycarbonyl-1,2,4,5-tetrahydro-3H-3-benzazepine (1.9 g) in pyridine (40 ml) cooled to 0°. Stirring was continued at room temperature for 18 hours. The solvent was removed by evaporation to give an oil which was taken up in methylene chloride, washed three times with aqueous sodium bicarbonate and three times with brine, then dried (Na$_2$SO$_4$) and evaporated in vacuo. The residue was purified by column chromatography on silica eluting with methylene chloride containing methanol (0% up to 5%). The product-containing fractions were combined and evaporated in vacuo to give a semi-solid which was triturated with ether to give the title compound, yield 1.2 g, m.p. 153°–154°.

Analysis %: Found: C,56.6; H,67.05; N,8.2; Calculated for C$_{16}$H$_{24}$N$_2$O$_4$S: C,56.45; H,7.1; N,8.2.

Preparation 21

7-Methanesulphonamido-1,2,4,5-tetrahydro-3H-3-benzazepine

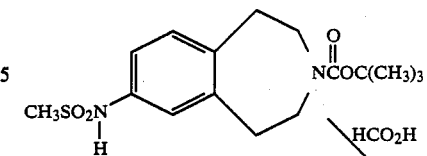

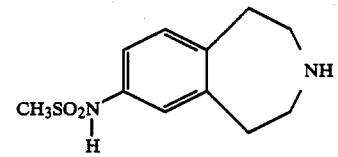

3-Tertiary-butoxycarbonyl-7-methanesulphonamido-1,2,4,5-tetrahydro-3H-3-benzazepine (0.6 g) and 98% formic acid (10 ml) were stirred together at room temperature for 2 hours. The solvent was evaporated in vacuo to give an oil which was basified with aqueous sodium bicarbonate. The aqueous solution was evaporated in vacuo and the residue was triturated with hot isopropanol. The isopropanol was decanted and evaporated in vacuo to give a solid which was recrystallised from ethyl acetate/hexane to give the title compound, yield 0.22 g.

Analysis %: Found: C,54.7; H,7.0; N,11.4; Calculated for C₁₁H₁₆N₂O₂S: C,55.0; H,6.7; N,11.7.

We claim:

1. A compound of the formula:

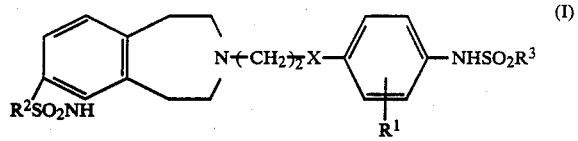

(I)

or a pharmaceutically acceptable salt thereof; wherein
R¹ is H, C₁–C₄ alkyl or C₁–C₄ alkoxy;
X is O,

or a covalent bond; and
R² and R³, which are the same or different, are each C₁–C₄ alkyl, with the proviso that when X is

R² and R³ are the same.

2. A compound as claimed in claim 1 wherein R¹ is H, methyl or methoxy.

3. A compound as claimed in claim 2 wherein R¹ is H.

4. A compound as claimed in claim 1, wherein R² and R³ are the same.

5. A compound as claimed in claim 2, wherein R² and R³ are the same.

6. A compound as claimed in claim 3, wherein R² and R³ are the same.

7. A compound as claimed in 1 wherein R² and R³ are methyl.

8. A compound as claimed in claim 2, wherein R² and R³ are methyl.

9. A compound as claimed in claim 3, wherein R² and R³ are methyl.

10. A compound as claimed in claim 1, wherein X is O or a covalent bond.

11. A compound as claimed in claim 2, wherein X is O or a covalent bond.

12. A compound as claimed in claim 3, wherein X is O or a covalent bond.

13. A compound as claimed in claim 4, wherein X is O or a covalent bond.

14. A compound as claimed in claim 5, wherein X is O or a covalent bond.

15. A compound as claimed in claim 6, wherein X is O or a covalent bond.

16. A compound as claimed in claim 1, said compound having the formula

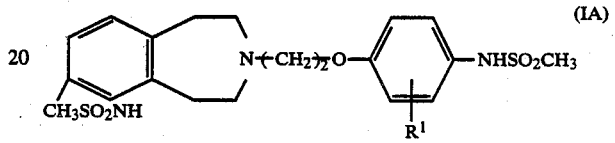

(IA)

or a pharmaceutically acceptable salt thereof.

17. A pharmaceutical composition comprising an antiarrhythmic effective amount of a compound as claimed in claim 1 and a pharmaceutically acceptable diluent or carrier.

18. A method of treating cardiac arrhythmias in mammals comprising administering to a mammal in need of such treatment an antiarrhythmic effective amount of a compound as claimed in claim 1.

19. A method according to claim 18, wherein said mammal is a human.

20. 7-Methanesulphonamido-3-(2-[4-methanesulphonamidophenoxy]ethyl)-1,2,4,5-tetrahydro-3H-3-benzazepine.

21. 7-Methanesulphonamido-3-(2-[4-methanesulphonamidophenyl]ethyl)-1,2,4,5-tetrahydro-3H-3-benzazepine.

* * * * *